United States Patent [19]

Coleman et al.

[11] Patent Number: 5,079,142
[45] Date of Patent: Jan. 7, 1992

[54] ORTHOGONAL FLOW IMMUNOASSAYS AND DEVICES

[75] Inventors: Patrick F. Coleman, Poway; Edward T. Maggio, San Diego, both of Calif.

[73] Assignee: Synbiotics Corporation, San Diego, Calif.

[21] Appl. No.: 6,662

[22] Filed: Jan. 23, 1987

[51] Int. Cl.⁵ ............... G01N 33/537; G01N 33/543
[52] U.S. Cl. ..................... 435/7.92; 422/55; 422/56; 422/57; 422/58; 422/61; 422/69; 435/970; 436/501; 436/514; 436/578; 436/538
[58] Field of Search ............... 436/501, 518, 538, 541, 436/514; 422/55–58, 60, 61, 69; 435/7, 7.92, 970

[56] References Cited

U.S. PATENT DOCUMENTS

| | | | |
|---|---|---|---|
| 3,888,629 | 6/1975 | Bogshawe | 436/542 X |
| 4,235,601 | 11/1980 | Deutsch et al. | 436/805 X |
| 4,366,241 | 12/1982 | Tom et al. | 435/5 X |
| 4,632,901 | 12/1986 | Valkirs et al. | 436/518 X |
| 4,670,381 | 6/1987 | Frickey et al. | 436/518 X |
| 4,753,775 | 6/1988 | Ebersole et al. | 422/69 X |
| 4,756,844 | 7/1988 | Hillman et al. | 422/81 X |
| 4,803,170 | 2/1989 | Stanton et al. | 436/518 |
| 4,861,711 | 8/1989 | Friesen et al. | 435/7 |
| 4,938,927 | 4/1990 | Kelton et al. | 422/64 |
| 4,943,522 | 7/1990 | Eisinger et al. | 435/7 |
| 4,981,786 | 1/1991 | Dafforn et al. | 435/7 |
| 5,006,474 | 4/1991 | Horstman et al. | 436/524 |

*Primary Examiner*—David Saunders
*Attorney, Agent, or Firm*—Edward S. Irons

[57] ABSTRACT

Methods and composition are provided for diagnostic assays, where a sample traverses a bibulous matrix in a first plane and the flow path redirected into a second plane at a binding site, where a signal is created in relation to the presence of analyte. Various protocols may be employed where components of a signal producing system may be combined with the sample, the matrix, or added at the binding site.

13 Claims, 2 Drawing Sheets

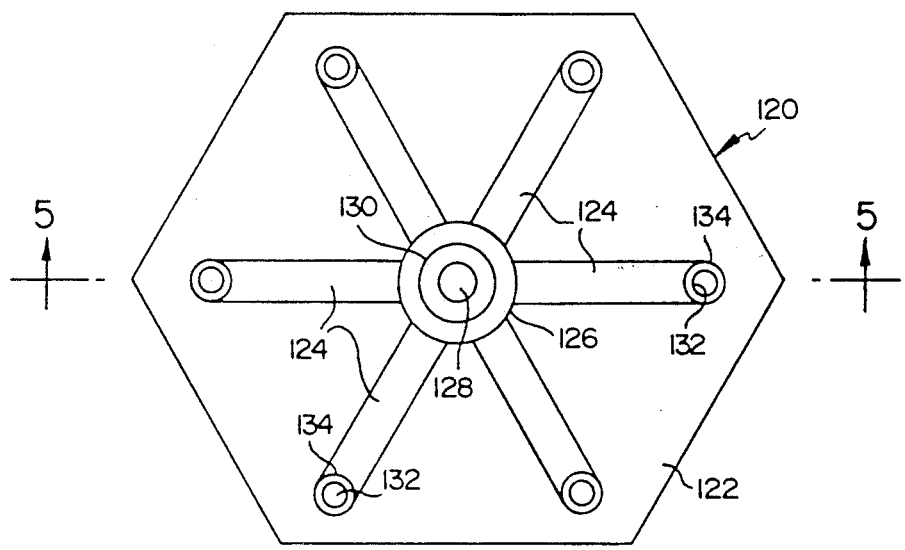
FIG. 4
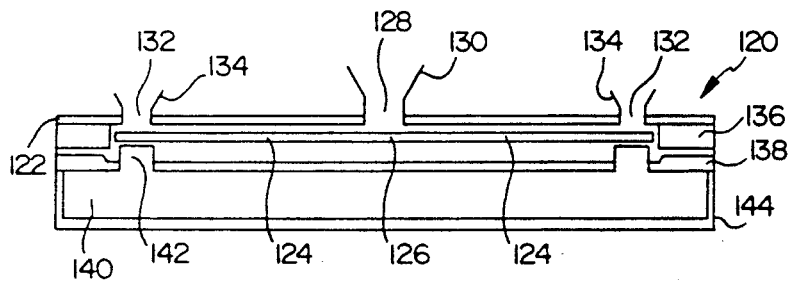
FIG. 5
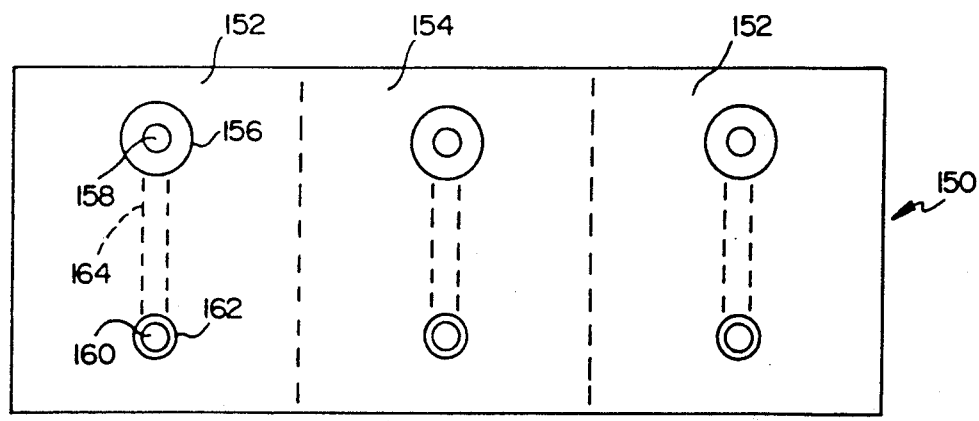

ORTHOGONAL FLOW IMMUNOASSAYS AND DEVICES

FIELD OF THE INVENTION

Diagnostic assays have found expanding applications in detecting a wide variety of drugs and other materials of interest. There have been continuing efforts to develop convenient devices and protocols which may be employed by untrained personnel, while providing for rapid, accurate results. Such devices require relatively simple equipment with minimal measurements and steps.

BACKGROUND OF THE INVENTION

Many areas of medicine, food processing, industrial processing and farming require the ability to detect the presence of a particular material. The need to measure the drug or other substance may be as a result of the abuse of drugs, the monitoring of therapeutic dosage, the detection of a pathogen, the detection of a diseased state, such as neoplasia, the detection of contaminants or pollutants, or the concentration of a particular component, as illustrative of the many situations which may be involved.

There has been an increasing interest to remove the requirement to measure a substance in the clinical laboratory and to measure the substance at the site where the information is to be used. This may include the doctors office, the home, the farm, the field or the processing plant. In this situation, there are many restrictions on the nature of the manner in which the determination is to be carried out. For the most part, the devices must be simple, rugged, and easily handled. The protocols should also be simple, and involve a minimal number of measurements of sample and reagent, preferably zero, minimal handling and number of reagents, as well as a small number of steps. In addition, the results should be easy to read, particularly being visually determined. In addition, there are other considerations such as preventing aerosolization, providing reagent stability, and the like.

The design of such devices therefore requires efforts to optimize the various requirements, without unduly interfering with other requirements. Thus, as a practical matter, the devices are only difficultly conceived and reduced to practice.

BRIEF DESCRIPTION OF THE RELEVANT LITERATURE

Commercially available devices designed for home and doctor use include the ICON device provided by Hybritech, the Abbott device and the Pacific Biotech device. Patent disclosures of interest include U.S. Pat. Nos. 4,435,504 4,540,659 and references cited therein.

SUMMARY OF THE INVENTION

Devices and methods are provided for determining a substance of interest, where orthogonal flow is provided, the sample medium migrating in a first plane, followed by migration in a second plane, while any reagents are directed in the second plane. The device includes one or more ports, a filter matrix, a binding pair member bound at an observation site, which site serves as the site of redirection of the flow path of the sample. One or more flow directing materials may be employed in conjunction with the matrix. In addition, an absorbant is provided for absorbing the sample medium and any additional media which are employed.

BRIEF DESCRIPTION OF THE DRAWINGS

FIG. 4 is a top view of a device providing for determining a panel of assays:

FIG. 5 is a cross-sectional view of the device of FIG. 4 along lines 5—5: and

FIG. 6 is a batch device depicting three individual devices joined together to carry out a plurality of assays.

DESCRIPTION OF THE SPECIFIC EMBODIMENTS

Figure 1:
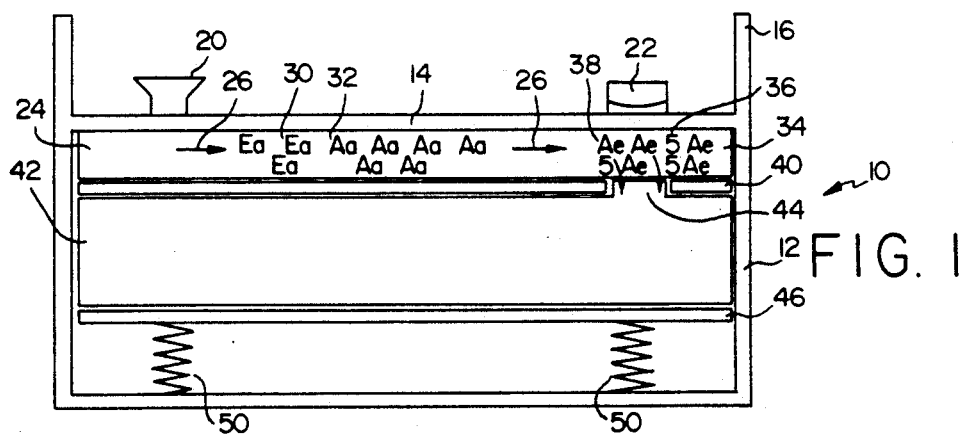
FIG. 1 is a side elevation cross-sectional view of an embodiment of this invention.

Methods and devices are provided which allow for a variety of protocols for the detection of substances. Depending upon the nature of the sample, the particular analyte, and the construction and organization of the device, the protocols may vary.

The method involves directing a sample medium in a first direction through a bibulous matrix providing for flow by capillarity. One or more manipulative steps may occur in the matrix. A binding zone is provided in the matrix proximal to the downstream end of the matrix opposite from the upstream end to which the sample medium is added.

The sample medium passes through the binding zone and is redirected into a plane substantially perpendicular to the plane of the matrix, where the sample medium and any liquids are absorbed, an absorbant serving as the receptacle for excess fluid. A labeled reagent is employed, which label provides for a detectable signal. The level of signal in the binding zone, usually a color signal, serves to indicate the presence and amount of the substance of interest, the analyte.

The bibulous material or matrix may serve a wide variety of functions. The matrix may serve to remove interfering materials for example, various matrices may serve to separate red blood cells and allow for the flow of serum free of the red blood cells and lytic contaminants. Various materials may be removed by employing reciprocal binding members, which selectively remove a particular substance present in the sample medium, including red blood cells or lytic components thereof. Beside removal of contaminants or other substances which may interfere with the detection of the signal, the bibulous matrix may also serve as a source of reagents which may react with the analyte or member of a signal producing system. Thus, the matrix or solutions may be used for providing the various components of a signal producing system involving the label.

In carrying out the assay, the sample may be used neat or may have been subject to prior treatment. The prior treatment may involve various means of separation, such as centrifugation, for removing red blood cells, chromatography, heating, buffering, as well as the addition of various reagents. A choice may be made between providing for one or more reagents in the sample as contrasted with providing for the reagents bound to the matrix.

The nature of the signal producing system, the costs of manufacturing, convenience, and other such considerations will determine whether the particular reagent is supplied bound to the matrix or is provided as a component to be added as part of the sample medium or as a subsequent reagent. Reagents can therefore be provided to be initially combined with the sample, as bound to the matrix, or added as a separate medium to the binding zone.

In carrying out the assay, the sample will be added proximal to one end of the matrix. Various techniques may be employed for directing the sample toward the other end of the matrix. During the traverse of the matrix, the sample may be subjected to interaction with various reagents. These reagents will be discussed in discussing the signal producing system. The sample traverses the matrix undergoing the appropriate interactions with the reagents present on the matrix until it encounters the binding zone. The binding zone will involve a specific binding pair member which will bind to a reciprocal binding pair member, which may include the analyte, in relation to the amount of analyte present in the sample. The binding zone is the reagent in which the signal is detected. The sample is then directed normal to the matrix to an absorbant which absorbs excess fluid.

The signal producing system may be varied widely, but will be subject to certain constraints. The signal producing system must provide a signal which is related to the presence of the analyte in the sample and in many situations will provide a semi-quantitative or quantitative signal. In most situations, the signal producing system should provide a signal which can be evaluated visually, rather than using instrumentation, although as appropriate, instrumentation may be employed. Therefore, while fluorescence, magnetic flux, ultra-violet light absorption, or other non-visual signal may be employed, for the most part, the signal producing system will provide a signal which is the result of absorption of light in the visual range by a dye. To this end, the signal producing system will usually employ an enzyme which catalyzes a reaction resulting in the formation or destruction of a dye absorbing light in the visual range. In these instances, the enzyme will be conjugated to a member of a specific binding pair.

The specific binding pair will consist of ligand and receptor, where the terms are somewhat arbitrary, although generally understood as to their meaning. The receptor, for the most part, will be a macromolecule which binds to a specific charge and spatial conformation, having a high affinity for such specific conformation as distinct from molecules having analogous but different charge and spatial conformations. For the most part, the receptors will be antibodies and therefore the assays are designated as immunoassays. However, other receptors may be employed, particularly naturally occurring receptors, which include enzymes, lectins, outer membrane proteins, such as T-cell receptors, growth factor receptors, MHC protein binding receptors, etc., or blood proteins, such as thyroxine-binding globulin, avidin, and the like. As a special case, the receptor may be a nucleic acid, where the nucleic acid may bind to a protein or a complementary single stranded sequence.

The ligand may be any molecule for which receptors are available or can be prepared. Usually, the ligand will be an organic molecule of at least about 100 daltons (D) and may involve macromolecules, aggregations, cells, viruses, or the like. For the most part, drugs will generally be of about 125 to 2000 molecular weight, oligopeptides and proteins will generally range from about 2 to 1000 kilodaltons (kD) and aggregates such as organelles, membrane fragments, viruses, or cells will be substantially larger.

The various analytes which may be detected in accordance with the subject invention are described in U.S. Pat. No. 4,261,968, which relevant disclosure is incorporated herein by reference.

The enzyme conjugate may take many different forms, depending upon the particular protocol which is employed. The enzyme conjugate may involve an enzyme conjugated to ligand or receptor, where the ligand or receptor is part of the specific binding pair involving analyte or may be a receptor which binds to the constant region of the immunoglobulin, such as an antibody to the $F_o$ *S. aureus* protein A, rheumatoid factor, or the like. The enzyme may be a holoenzyme, apoenzyme, or enzyme fragment, where the fragment is capable of combining with a second fragment to provide a protein product having enzymatic activity.

Various combinations of reagents can be employed. Constraints on the combinations of reagents in a particular medium and the timing of bringing the reagents together will include interactions between the reagents, for example, reaction of substrate with enzyme, stability of the reagent, the time required for reaction, control of the amount of the reagent, and the like. For example, with an antigen analyte, one could provide for anti-antigen bound to the matrix at the binding site. One could then provide for enzyme-(anti-antigen) conjugate as a separate reagent, with enzyme substrate as a third reagent.

Alternatively, one could provide for an enzyme acceptor fragment at the binding site, which would serve as the receptor for the enzyme donor fragment. See for example, U.S. Pat. No. 4,378,428 and PCT/US85/02095 modified. The S peptide fragment of ribonuclease A or CNBr2 fragment of β-galactosidase may be conjugated with the analyte or a competitive fragment thereof. The sample could then be added to the reagent which would include the enzyme fragment conjugate and the substrate for the enzyme. The matrix would include in a first zone, anti-analyte, while the binding zone will include the enzyme acceptor fragment.

Another alternative is employing the channeling reaction as is described in U.S. Pat. No. 4,233,402. In this embodiment, a combination of enzymes is used, where the product of one enzyme is the substrate of the other enzyme. In this embodiment, the sample could be combined with a second-enzyme-(anti-antigen) conjugate and substrate for the first enzyme. The matrix would include anti-antigen and first enzyme in the binding region.

Various enzymes may be used in the signal producing system. The enzymes may be used individually or in combination, such as β-galactosidase, malate dehydrogenase, glucose-6-phosphate dehydrogenase, acetylcholinesterase, alkaline phosphatase, glucose oxidase, horse radish peroxidase, urease, etc.

Substrates which may find use include: umbelliferyl phosphate, galactosidyl fluorescein, tetramethylbenzidine, tetrazole salts, ABTS, or the like.

In addition, other reagents may be bound to the matrix, either diffusively or non-diffusively, such as receptors, enzymes, enzyme substrates, ligands, etc. These various materials may be bound in the binding zone or as reagents upstream from the binding zone, where the diffusively bound reagents may migrate from the upstream region to the binding zone region.

Kits can be provided with the various reagents which may be used in conjunction with the device. The kits may include the various conjugates described above, such as the enzyme-(anti-antigen) conjugate, the analyte-(enzyme fragment) conjugate, the anti-antigen and anti(anti-antigen)-conjugate, reagents such as buffers, substrates for the enzyme, the matrix, or the like.

The matrix may be any bibulous material which provides for transport of an aqueous medium by capillarity, as well as binding of the desired reagents. In addition, the matrix will desirably minimize the amount of non-specific binding in the binding zone and may provide for ancillary properties, such as separation of red blood cells, removal of particulate matter, chromatographic separation, or the like.

Various materials may be used, both cellulosic and non-cellulosic, and these include glass fibers, particularly in the range of about 0.2 to $5\mu$, cellulose, nitrocellulose, paper, silica gel, etc. The matrix will generally be at least about 2 mm wide and usually not more than about 1 cm wide, generally being at least about 0.5 cm long and not more than about 5 cm long, usually not more than about 3 cm long.

As already indicated, the matrix will have a binding zone which can be any convenient shape or formation and will serve as the site at which the signal is observed.

Various protocols may be employed for performing the assay. A few protocols are provided as illustrative of different combinations of steps and reagents for carrying out the assay. These illustrative protocols are not intended to be exhaustive, but rather illustrative of particular embodiments.

In the first protocol to be described, the binding zone has anti-antigen as a capture antibody. The binding zone is positioned under a reagent addition and viewing port. Sample medium is added to the matrix at a position distant and upstream from the binding zone and allowed to wick through the filter matrix while directed to the binding zone. The sample traverses the matrix to the binding zone in a first direction and is then directed through the binding zone to an absorbing layer in a direction normal to the first direction. Any analyte, in this case antigen analyte, present in the sample will be captured in the binding zone by the capture antibody. In some applications it may be beneficial to filter the conjugate and/or other reagents through the orthogonal matrix before contacting the immunochemical surface, rather than adding them directly into the reagent addition (test) port.

The binding zone is then washed with a wash solution through the reagent addition port, followed by the addition of enzyme-(anti-antigen) conjugate through the reagent addition port. At this point, the reaction may be allowed to incubate followed by addition of a wash solution to remove any non-specifically bound conjugate. The developing solution is hen added containing all of the reagents necessary for the enzyme reaction to provide for a visual signal.

The individual wash solutions are optional, depending upon the nature of the sample, the amount of interference that may be expected from sample components, the amount of residual conjugate which may be retained in the binding zone, and the like. For example, it may be found that the substrate solution suffices to remove any non-specifically bound enzyme conjugate, so as to substantially minimize the background signal. Also, it may be found that the sample does not include any components which interfere with the binding reactions between the specific binding pair members, nor with the development of the signal.

A second alternative protocol employs a zone upstream from the binding zone where the enzyme conjugate is diffusively bound to the matrix. Addition of the sample to the matrix results in traversing the enzyme conjugate zone and carrying the enzyme conjugate with the sample to the binding zone. The binding zone may then be washed as described above, followed by addition of the development solution. As indicated above, the wash solution is optional, depending upon the nature of the sample, the amount of sample, and the background signal resulting from non-specifically bound conjugate.

In a third protocol, one may employ the channeling effect by having a first enzyme bound to the matrix in the binding zone. As previously indicated, the first enzyme produces a product which is the substrate of the second enzyme. The second enzyme produces a product which provides for a visual signal. In this protocol, the sample is added to a reagent containing second enzyme-(anti-antigen) conjugate, all of the necessary components of the enzyme reactions for both the first and the second enzymes, except for the product of the first enzyme, and any buffers or other reagents to optimize the development of the visual signal. The sample may then be added to the matrix at a site distant from the binding zone and allowed to traverse to the binding zone. The antigen may act as a bridge binding the second enzyme to the binding zone by binding to anti-antigen in the binding zone. Rather than have the enzyme substrates together with the second enzyme-(anti-antigen) conjugate, one may add them separately through the port as previously described after the sample has passed through the binding zone.

Where a hapten is the analyte, rather than an antigen or receptor, the assay may be modified by having hapten present in the binding zone. The sample may then be contacted with second enzyme-(anti-hapten). To the extent that the binding sites of the conjugate are filled with the hapten in the sample, the conjugate will be unable to bind to the hapten present in the binding zone. Thus, the amount of second enzyme present in the binding zone will be related to the amount of hapten in the sample.

An alternative technique is to use an enzyme fragment, which may complex with another enzyme fragment to provide for an enzymatically active protein. For example, one may prepare a conjugate of the S-peptide of ribonuclease A, while binding the S-protein in the binding zone of the matrix. Anti-antigen may be bound in a region upstream from the binding zone, which is traversed by the sample. By combining the sample with the S-peptide conjugate, the amount of S-peptide conjugate which exits from the anti-antigen region will be related to the amount of antigen in the sample. The S-antigen conjugate which exits from the anti-antigen region will bind to the S-protein in the binding zone. One may then add enzyme substrate to the binding zone through the reagent addition port to detect any active enzyme.

In another protocol, one can provide for a series of regions in the matrix. A first region would include antigen-(enzyme conjugate) diffusively bound to the matrix. A second region would include anti-antigen. The binding region would be anti-enzyme. The sample medium would be introduced upstream from the regions, so as to first traverse the enzyme-antigen conjugate which would be carried with the sample into the anti-antigen region, where antigen and enzyme-antigen conjugate would compete for the binding sites of the anti-antigen. Any enzyme-antigen conjugate which exited from the anti-antigen region would be captured by the anti-enzyme present in the binding zone. Once again, by adding a developer solution to the binding zone, the amount of signal produced would be related to the amount of analyte in the sample.

While the protocols have been described for haptens and antigens, it is well known in the art to carry out analogous protocols with receptors. In the case of receptors, one would normally reverse the role of the receptor with the antigen and vice versa.

Means may be provided for directing the flow of the sample solution through the matrix linearly and to the region of the binding zone, where the binding zone may assume a wide variety of configurations. Thus, the path of the sample may be controlled as to direction and rate of flow.

In addition, the matrix may be provided with a control zone, which will be associated with the binding zone, usually in close spatial juxtaposition with the binding zone. The control region will provide for a signal which may be compared with the signal produced in the binding zone. The control region may provide for a fixed amount of enzyme bound to the matrix, which will produce a signal level associated with an amount of analyte in the range of interest. Alternatively, one could provide for an amount of anti-enzyme, which would bind enzyme conjugate at a predetermined level to provide a signal associated with an amount of sample in the range of interest. This approach would be particularly useful in sandwich assays, where the enzyme conjugate is in excess over the amount to be bound to the surface in the binding zone. The control zone may be contiguous to the binding zone, separated from the binding zone, involved with forming patterns with the binding zone, or the like.

For some applications, it may be desirable to have a plurality of determinations carried out simultaneously or consecutively with a single unit. For example, one could provide for an apparatus having a hub with a plurality of spokes providing for the path of the sample. The sample would introduced at the hub and would radiate from the hub along the plurality of paths, each path could be treated with one or more different reagents, so as to allow for detection of different analytes present in the sample. In this manner, a single sample could be analyzed for a family of analytes, such as drugs of abuse, pathogens, or the like. In other situations, it may be desirable to have a single apparatus incorporating a plurality of units, which may be used with the same or different samples and be carried out simultaneously. Thus, the various samples would be subjected to the same conditions. This could be particularly useful if one wishes to employ a single control under the same conditions to which the sample is subjected. Conveniently, the various units could be joined together in a manner where they could be used either as a single unit or separated one from the other to provide for individual independent units.

For further understanding of the invention, the figures will now be considered.

In FIG. 1, a prototypic device (10) is depicted. The device has a container (12) which includes a cover (14), which is disposed below the top (16) of the container wall. The cover has a sample addition port (20) and a lens (22) for viewing. Below the cover (14) is a matrix (24), which matrix serves as the transport mechanism for transporting the sample by capillary action across the matrix in the direction of the arrows (26). The matrix (24) also serves to bind reagents, the reagents may remain bound to a particular region or may be carried with the moving front of the sample medium across the matrix (24).

In the particular embodiment depicted in FIG. 1, the matrix contains enzyme-antigen conjugate (30) indicated as Ea, antibody to antigen (32) indicated as Aa as a zone downstream from the enzyme-antigen conjugate (30) and the binding zone (34) which includes antibody to enzyme (38) depicted as Ae and substrate for the enzyme (36) indicated as S. Immediately beneath the matrix (24) is water impermeable layer (40) which serves to separate the matrix (24) from the absorbant (42). Various absorbants may be used, such as cellulose, Filtrona, cotton, talc, silica gel, and the like. The absorbant may be a sponge-like material, powder, gel or other material which may absorb liquid from the matrix (24) and serve as a receptacle for excess liquid. The absorbant (42) has protuberance (44) which is in direct contact with the matrix (24) so as to allow for flow from the binding zone (34) into the absorbant layer (42). Platform (46) can be supported by springs (50), if necessary, or other compressible structures in order to maintain the assembly under moderate pressure urging the assembly toward cover (14).

In carrying out the assay, the sample medium would be introduced through port (20), where the sample medium would be transported by capillary action in the direction indicated by arrow (26). As the sample medium passed the region containing the enzyme-antigen conjugate, the conjugate would be dissolved into the sample medium and transported with the sample medium front. The sample medium would then traverse the anti-antigen region where antigen in the sample medium would compete with antigen in the enzyme-antigen conjugate for the available binding sites of the anti-antigen. Depending upon the amount of antigen in the sample, enzyme-antigen would exit the anti-antigen region and continue to the binding region (34). Any enzyme-antigen conjugate in the medium would be captured by the anti-enzyme, which is non-diffusively bound. The substrate would dissolve into the medium and react with the enzyme present in the binding region producing a product which would strongly bind to the matrix (24). The product would be darkly colored, for example, black, and would produce a dark spot over a predetermined time period, where the absorption of the spot would be related to the amount of antigen in the sample. One would view the spot through lens (22), so as to get a qualitative determination of the presence and amount of antigen in the sample.

Figure 2:
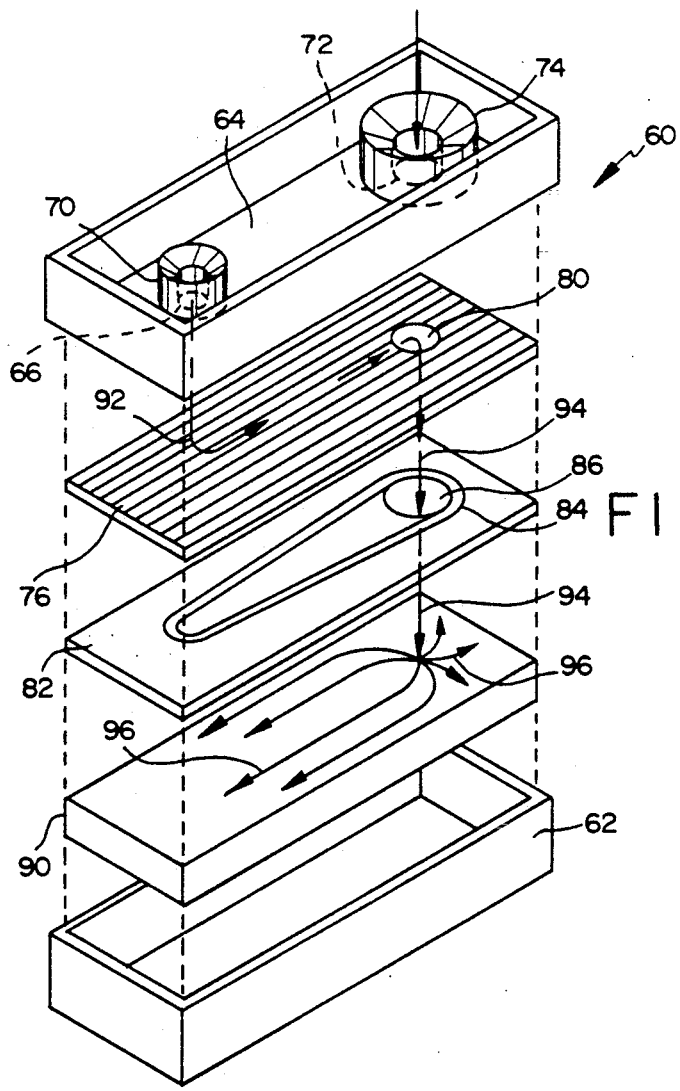
FIG. 2 is an expanded perspective view of a second embodiment of this invention.

In FIG. 2 another embodiment is depicted. This device (60) has a container (62). The container (62) has top closure (64). Top closure (64) has port (66) into which sample receptacle (70) feeds a sample. Top closure (64) has a second port (72) into which reagent and wash solution receptacle (74) feeds the appropriate liquid media. Pressed against top closure (64) is filter matrix (76) with binding region (80). The filter matrix (76) is incorporated into a thin flow direction separator (82). Such separators can be illustrated by the following examples.

1. The separator could have the filter matrix (76) inserted into a raised lip (84) which contains the filter matrix and, effectively, directs the flow of sample fluid to the binding region (80). The separator has orifice (86) through which the sample flows from the binding region through a unidirectional flow film (89). The absorbant matrix (90) which contacts the unidirectional flow film (89) receives the excess fluid and withdraws the fluid from the filter matrix (76).

2. The separator, alternatively, could be constructed from three laminated plastic sheets, with the middle layer cut out in a shape to match the filter matrix (76) (not shown). The top sheet contains the sample addition port (equivalent to 66) and the top test port (equivalent to 72). The bottom sheet contains the exit test port (equivalent to 86) and makes intimate contact with the unidirectional flow film (89). the unidirectional flow film in turn makes intimate contact with the absorbant matrix (90).

An assay may be carried out, for example, by combining sample containing analyte, for example antigen, with enzyme-antigen conjugate and adding it to receptacle (70). The sample then passes through port (66) and proceeds in the direction of arrows (92) into the filter matrix (76), where it is directed by separator (82) toward the binding region (80). The sample medium passes through the binding region (80) and proceeds in the direction of arrow (94) to absorbant (90), where the liquid spreads out as indicated by arrows (96). Antibody in the binding region (80) captures enzyme-antigen conjugate in proportion to the amount of antigen present in the sample. After the sample has been exhausted, so that no further sample remains in the sample receptacle (70), a wash solution may be added to receptacle (74) to wash away any non-specifically bound enzyme-antigen conjugate. When the receptacle (74) is empty, a substrate solution may be added to fill the receptacle and the substrate solution allowed to traverse through the binding region (80) to be absorbed by absorbant (90). The binding region (80) may then be viewed through port (72), where the presence of color is indicative of the presence of analyte.

Alternatively, rather than combine the antigen with an enzyme-antigen conjugate, one could first allow the sample to traverse the matrix and pass through the binding region, filling up a proportional number of binding sites. One could then add enzyme-antibody conjugate which would bind to antigen captured by antibody in the binding region. The procedure would then follow as described above.

Figure 3:
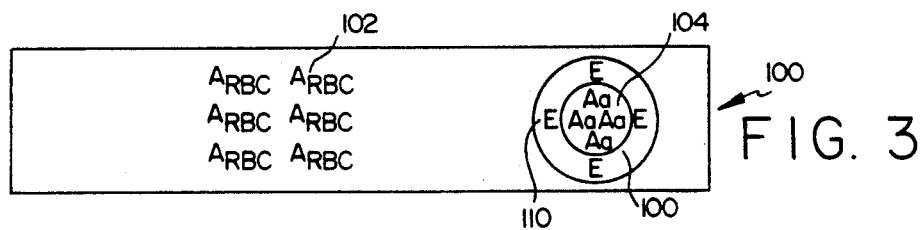
FIG. 3 is a plan view of a matrix strip according to the invention.

In FIG. 3, is depicted an alternate form of a matrix (100). In this matrix, antibodies to red blood cells (102) are bound to the matrix indicated at $A_{rbc}$. Where blood is employed as a sample, the antibodies (102) will serve to remove the red blood cells from the traveling sample medium, so that any red blood cells will not interfere with the detection of color in the binding region (104). The binding region (104) is indicated as a circle, but any design may be employed, such as a bar, cross, triangle, or the like. Surrounding the binding region (104) is control region (106). Control region (106) has a predetermined amount of enzyme (110) indicated as E. By performing the assay as described above, the amount of enzyme conjugate bound to the binding region will be related to the amount of antigen in the medium. By comparing the color produced in the binding region with the color produced in the control region, one can determine whether the amount of antigen in the sample exceeds a predetermined level. This will be particularly useful, where the result is either positive or negative, depending upon whether the analyte is above a predetermined level.

FIGS. 4 and 5 depict a device which may be used for determining a panel of drugs so that a single sample may be treated in a variety of ways to give a variety of results. Panel device (120) is a filter top plate (122) under which appears a plurality of matrixes (124). The individual matrixes may be of the same or different lengths, as required. The matrixes are joined at a central hub region (126). The hub region contacts each of the filter matrices (124) and feeds the sample into each matrix. Inlet (128) connects well (130) to the hub (126). The well (130) allows for a measured amount of sample to be added to the well which will then be absorbed into the hub region (126) and be transmitted evenly to the various filter matrices (124). A plurality of reagent addition ports (132) are provided which intimately contact the ends of each matrix (124). Ports (132) are surrounded by a well (134) which allows for the introduction of various reagents through the port. The matrix is retained in plate (136), where plate (136) has been cut out to house matrices (124) and hub (126) and further act as a divider between the matrices (124). The plate (136) is supported by separator plate (138) which intimately contacts a unidirectional flow membrane (139), which in turn intimately contacts absorbant material (140). The absorbed fluid components are retained in housing (144).

In FIG. 6, multiple unit (150) has a plurality of devices (152) joined together at broken lines (154) indicating the presence of a fracture line, allowing for separation of the individual units, if desired. As in the previous units, there is a sample well (156) in the port (158) and a reagent port (160) with well (162) where the filter matrix (164) is indicated by the broken lines.

As is evident from the above description, the subject devices and protocols provide for a large number of advantages. As contrasted to other devices which are commercially available, in accordance with the subject invention the sample may be pre-treated without the necessity for physical removal of a pretreatment filter, thus avoiding aerosolization of infectious or potentially infectious samples. Filtration of sample parallel to the thin dimension of the filter matrix as opposed to perpendicular to the filter matrix as is currently being done or has been depicted in the literature allows for the physical separation of blood cells using selected materials, such as glass fiber filters or filter matrix containing binding ligands, which inhibit the migration of the red blood cells. The sample may be filtered through a much longer linear dimension of filter material prior to arriving at the binding region. The filter matrix can be utilized to allow administration, mixing and reaction of immunological components or other pre-treatment components without physical manipulation of these materials. Thus, user steps may be eliminated from the assay protocol for greater convenience and test reliability. In the subject devices, the matrix serves as a useful medium for stabilizing dried immunological and pretreatment reagents in the assay device. Since such dried materials are typically more stable than materials provided in liquid form, the devices are more amenable to long shelf life or storage at elevated temperatures. This is a particularly important feature for an over-the-counter or consumer-oriented product or for general field use where refrigeration is impractical. In addition, the nature of the filter may be varied in order to allow modulation of the migration time across the matrix to the binding region. This provides a means for controlling the time of the immunological reactions or pretreatment reactions which can be provided for with the filter matrix.

By providing for a long path flow of fluids, one can allow the sample to traverse a filter matrix over a relatively long path, or providing for a short path to the binding region for reagents and wash solutions, where the reagents may be provided at a substantially constant concentration to the binding region. The long path of the sample provides for removal of interfering materials in an efficient manner. The short path for the wash solutions and reagent provides economies in time, improved control of the contact between reagents, such as conjugates and developer solutions, and may reduce the amount of solution required for obtaining the desired result.

Multiple test devices allow for performing a panel of related tests on a single specimen or a series (batch) of the same tests on a group of different samples. Multiple test devices provide cost economics in decreasing the cost per reportable result.

Although the foregoing invention has been described in some detail by way of illustration and example for purposes of clarity of understanding, it will be obvious that certain changes and modifications may be practiced within the scope of the appended claims.

What is claimed is:

1. A device for the detection of an analyte comprising:
   a matrix in a first plane providing for capillary transport of an aqueous sample medium;
   cover means positioned over said matrix, a first port in said cover means, with said first port positioned over said matrix for directing said sample medium to a first site on said matrix;
   flow means in contact with said matrix at a second site on said matrix for directing flow of said sample medium at said second site to a second plane substantially parallel to said matrix in said first plane, said flow through said flow means being substantially perpendicular to said matrix;
   a immunoglobulin bound to said matrix at said second site; and
   absorbant means, in contact with said flow means, for receiving said sample medium in said second plane.

2. A device according to claim 1, including a second port in said cover situated over said second site for directing fluids through said second site and said flow means to said absorbant means.

3. A device according to claim 2, including directing means on a separator support, said separator support substantially parallel to and under said matrix, said directing means in contact with said matrix for linearly directing sample medium from said first site to said second site.

4. A device according to claim 3, wherein said directing means includes a raised lip from said separator support to direct said sample medium to said second site.

5. A device according to claim 3, including spring means for urging said matrix, said flow means and said absorbant toward each other in order to maintain intimate contact.

6. A device according to claim 1, including at least one of:
   (a) a second port in said cover means, said second port situated over said second site for directing fluids through said second site and said flow means to said absorbant means;
   (b) direction means on a separator support, said separator support substantially parallel to and under said matrix, said directing means in contact with said matrix for linearly directing said sample medium from said first site to said second site; or
   (c) spring means for urging said matrix, said flow means and said absorbant means toward each other in order to maintain intimate contact.

7. A device according to claim 1, including a first receptacle on said cover means, said receptacle having an open bottom communicating with said first port.

8. A device according to claim 7, including a second port in said cover means, said second pot situated over said second site for directing fluids through said second site and said flow means to said absorbant means, and a second receptacle on said cover means having an open bottom communicating with said second port.

9. A multiunit device for the detection of at least one analyte comprising a plurality of containers, each container sharing at least one common wall with an adjacent container, each container comprising:
   a matrix in a first plane providing for capillary transport of an aqueous sample medium;
   cover means positioned over said matrix, a first port in said cover means, with said first port positioned over said matrix for direction said sample medium to a first site on said matrix;
   flow means in contact with said matrix at a second site on said matrix for directing flow of said sample medium at said second site to a second plane substantially parallel to said matrix in said first plane, said flow through said flow means being substantially perpendicular to said matrix;
   an immunoglobulin bound to said matrix at said second site; and
   absorbant means, in contact with said flow means, for receiving said sample medium in said second plane.

10. A device for the detection of an analyte comprising:
    a container including a cover;
    a bibulous matrix in a first plane providing for capillary transport of an aqueous sample medium, said bibulous matrix in said container and under said cover;
    a first port in said cover, said first port positioned over said bibulous matrix for directing said sample medium to a first site on said matrix;
    flow means in contact with said matrix at a second site on said matrix for directing flow of said sample at said second site to a second plane substantially parallel to said bibulous matrix in said first plane, said flow through said flow means being substantially perpendicular to said bibulous matrix;
    an immunoglobulin bound to said bibulous matrix at said second site; and
    absorbant means, in contact with said flow means, for receiving said sample medium in said second plane.

11. A device according to claim 10, wherein said immunoglobulin is an antibody to analyte.

12. A device according to claim 10, wherein and immunoglobulin is an antibody to an enzyme.

13. A device according to claim 11, including at least one of:
    (a) a second port in said cover means, said second port situated over said second site for directing fluids through said second site and said flow means to said absorbant means;

(b) direction means on a separator support, said separator support substantially parallel to and under said matrix, said direction means in contact with said matrix for linearly direction said sample medium from said first site to said direction site; or (c) spring means for urging said bibulous matrix, said flow means and said absorbant means toward each other for making intimate contact.

* * * * *